United States Patent
Son (10) Patent No.: US 10,195,240 B2
(45) Date of Patent: Feb. 5, 2019

(54) COMPOSITION FOR PREVENTING OR TREATING OXIDATIVE BRAIN DAMAGE AND BRAIN DYSFUNCTION, AND PRODUCTION METHOD FOR SAME

(71) Applicant: Daejeon University Industry-University Cooperation Foundation, Daejeon (KR)

(72) Inventor: Chang Gue Son, Daejeon (KR)

(73) Assignee: Daejeon University Industry-University Cooperation Foundation, Daejeon (KR)

( * ) Notice: Subject to any disclaimer, the term of this patent is extended or adjusted under 35 U.S.C. 154(b) by 346 days.

(21) Appl. No.: 14/653,873

(22) PCT Filed: Dec. 27, 2012

(86) PCT No.: PCT/KR2012/011532
§ 371 (c)(1),
(2) Date: Jun. 19, 2015

(87) PCT Pub. No.: WO2014/098295
PCT Pub. Date: Jun. 26, 2014

(65) Prior Publication Data
US 2015/0328271 A1    Nov. 19, 2015

(30) Foreign Application Priority Data
Dec. 20, 2012 (KR) .................. 10-2012-0149926

(51) Int. Cl.
*A61K 36/481* (2006.01)
*A61K 36/537* (2006.01)
*A23L 33/105* (2016.01)

(52) U.S. Cl.
CPC .......... *A61K 36/481* (2013.01); *A23L 33/105* (2016.08); *A61K 36/537* (2013.01); *A23V 2002/00* (2013.01)

(58) Field of Classification Search
CPC ........................... A61K 36/481; A61K 36/537

USPC ................................................ 424/746, 757
See application file for complete search history.

(56) References Cited

U.S. PATENT DOCUMENTS

| 2007/0053999 A1 | 3/2007 | Wei et al. |
| 2009/0162459 A1 | 6/2009 | Shi et al. |
| 2012/0070407 A1 | 3/2012 | Lazdunski et al. |

FOREIGN PATENT DOCUMENTS

| CN | 1742968 A | * | 3/2006 |
| CN | 101618176 A | * | 1/2010 |
| KR | 100950164 B1 | | 3/2010 |
| KR | 1020110130144 A | | 12/2011 |
| WO | 2010110755 A1 | | 9/2010 |

OTHER PUBLICATIONS

Lee et al "Myelophil ameliorates brain oxidative stress in mice subjected to restraint stress", Progress in Neuro-Psychopharmacology & Biological Psychiatry, Jul. 17, 2012, vol. 39, pp. 339-347.*
Lee, J.-S. et al., "Myelophil ameliorates brain oxidative stress in mice subjected to restraint stress" Progress in Neuro-Psychopharmacology & Biological Psychiatry, Jul. 17, 2012, vol. 39, pp. 339-347.
Son, Hye Young et al., "Neuroprotective effect of modified Boyanghwano-Tang and the major medicinal plants, Astragali Radix and Salviae Miltiorrhizae Radix on ischemic stroke in rats", The Society for Herbal, Jun. 2010, vol. 25, No. 2, pp. 71-79. (English-language abstract included).

* cited by examiner

Primary Examiner — Christopher R Tate
Assistant Examiner — Deborah A Davis
(74) Attorney, Agent, or Firm — The Webb Law Firm

(57) ABSTRACT

Provided is a composition for preventing or treating oxidative brain injury and brain dysfunction including an extract of *Astragali* Radix and *Salvia Miltiorrhizae* Radix as an active ingredient, the composition having a highly outstanding preventive or therapeutic effect in animal models simulating brain-tissue damage and brain dysfunction induced by acute and long-term excessive stress generated in actual clinical practice, which is effectively usable as a therapeutic agent thereof.

5 Claims, 8 Drawing Sheets

COMPOSITION FOR PREVENTING OR TREATING OXIDATIVE BRAIN DAMAGE AND BRAIN DYSFUNCTION, AND PRODUCTION METHOD FOR SAME

CROSS-REFERENCE TO RELATED APPLICATIONS

This application is the United States national phase of International Application No. PCT/KR2012/011532 filed Dec. 27, 2012, and claims priority to Korean Patent Application No. 10-2012-0149926 filed Dec. 20, 2012, the disclosures of which are hereby incorporated in their entirety by reference

TECHNICAL FIELD

The present invention relates to a composition for preventing or treating oxidative brain damage and brain dysfunction including an extract of *Astragali* Radix and *Salvia Miltiorrhizae* Radix as an active ingredient, a preparation method thereof, and a food composition for improving or preventing oxidative brain damage and brain dysfunction including the extract as an active ingredient.

BACKGROUND ART

In accordance a recent rapid industrialization and aging phenomenon of modern society, brain-related diseases have become a major issue in addition with an increase in various other diseases. A representative cause of the brain-related diseases may be excessive stress. The excessive stress is inevitable in accordance with rapid industrialization and development of the modern society, which induces progression of brain dysfunction such as insomnia, depression, attention disorder, memory loss, oxidative damage, and aging, such that Alzheimer syndrome, Parkinson syndrome, Huntington syndrome, and functional disorders of a brain tissue have prevalently and gradually increased, and accordingly, social costs also have steadily increased.

In general, the damage to the brain tissue due to excessive stress primarily causes a torpor state as physical response and kills cells configuring various parts of the brain, particularly hippocampus to block neurotransmission paths toward cerebrum, thereby inducing various brain dysfunctions (behavioral disorder and memory loss), and promotes secretion of stress hormone due to excessive activation of an HPA axis (hypothalamic-pituitary-adrenal axis) caused by stress reaction. The secretion of the stress hormone secondarily results in excessive occurrence of reactive oxygen species (ROS) and a lack of an antioxidant system (glutathione system, superoxide dismutase, and catalase) which is a defense mechanism removing the reactive oxygen species and even results in constraining physical activity due to a complex dysfunction of the brain tissue.

Clinically, the most important step affecting condition of a patient at various stages of oxidative brain damage and brain dysfunction induced by excessive stress and a progression of the diseases is to inhibit damage to hippocampus, or is to inhibit progression of liver cirrhosis if the damage to hippocampus already starts. Therefore, most of a number of researchers studying treatment of oxidative brain damage and brain dysfunction have made an effort to prevent such diseases and to develop therapeutic agents. Nevertheless, there are still no special treatment or medications.

Due to an effort to develop various drugs (Acetyl-L-Carnitine-HCl and MAO, PNMT and COMP inhibitor) globally and secure scientific basis thereof so as to solve the above-described problems, a partial efficacy in improving metabolism and inflammation of stress hormone has progressed, however, fundamental solutions in view of stability and accurate action mechanism of the drugs still remain.

As a result of studying and experimenting with various combinations of medicinal herb compositions in animal models suffering from damage to brain tissue and brain dysfunction induced by oxidative brain tissue damage, the present inventors found that an extract of *Astragali* Radix and *Salvia Miltiorrhizae* Radix was effective in preventing and treating damage to the brain tissue and the brain dysfunction, and completed the present invention.

DISCLOSURE

Technical Problem

An object of the present invention is to provide a composition for preventing or treating oxidative brain damage and brain dysfunction.

Another object of the present invention is to provide a preparation method of a composition for preventing or treating oxidative brain damage and brain dysfunction.

Another object of the present invention is to provide a food composition for improving or preventing oxidative brain damage and brain dysfunction.

Technical Solution

In one general aspect, a composition for preventing or treating oxidative brain damage and brain dysfunction includes an extract of *Astragali* Radix and *Salvia Miltiorrhizae* Radix as an active ingredient.

In another general aspect, a preparation method of a composition for preventing or treating oxidative brain damage and brain dysfunction includes: extracting a mixture of *Astragali* Radix and *Salvia Miltiorrhizae* Radix with 10 to 70% ethanol; and lyophilizing the extract.

In another general aspect, there are provided a food composition for preventing or improving oxidative brain damage and brain dysfunction including an extract of *Astragali* Radix and the *Salvia Miltiorrhizae* Radix as an active ingredient, and a preparation method of the food composition.

Hereinafter, the present invention will be described in detail.

The present invention relates to a composition for preventing or treating oxidative brain damage and brain dysfunction including an extract of *Astragali* Radix and *Salvia Miltiorrhizae* Radix as an active ingredient.

It is known that *Astragali* Radix is a herbal medicine belonging to Leguminosae, and is a plant used for fragile or dropsy as relaxation, sthenia, anhidrotic, diuretic drug, and the like, and having vasodilation and hypotensive functions. It is known that *Salvia Miltiorrhizae* Radix is a herbal medicine belonging to Ladiatae, containing Tanshinone, and the like, as main ingredients, and used for menstruation, uterine bleeding, abdominal pain, and the like, as sthenia drug, hemagogue drug, and a drug for women's diseases.

There is no applied research into oxidative brain damage and brain dysfunction using *Astragali* Radix and *Salvia Miltiorrhizae* Radix in the related art. However, in the present invention, it was found that the extract of *Astragali* Radix and *Salvia Miltiorrhizae* Radix has excellent efficacy in inhibiting and treating occurrence and progression of the oxidative damage to brain tissue and brain dysfunction.

The extract of *Astragali* Radix and *Salvia Miltiorrhizae* Radix in the present invention is effective in preventing or treating oxidative damage to brain and brain dysfunction due to stress. In an exemplary embodiment of the present invention, when the composition according to the present invention is administered to an experimental group suffering from brain damage due to acute and chronic stress, an improvement in an antioxidant system in blood and brain tissue, and significant improvement in the dysfunction of related hormones and memory impairment are shown.

In the composition for preventing or treating the oxidative brain damage and the brain dysfunction including the extract of *Astragali* Radix and *Salvia Miltiorrhizae* Radix as an active ingredient according to the present invention, the active ingredient may be Astragaloside IV, Formononetin, Rosmarinic acid, or Salvianolic acid B.

In addition, the oxidative brain damage and the brain dysfunction may be at least any one selected from the group consisting of dementia, Alzheimer syndrome, Parkinson syndrome, and Huntington syndrome.

The extract of *Astragali* Radix and *Salvia Miltiorrhizae* Radix included in the composition of the present invention may be prepared by mixing *Astragali* Radix with *Salvia Miltiorrhizae* Radix before extraction and extracting *Astragali* Radix and *Salvia Miltiorrhizae* Radix.

With respect to a weight ratio between the *Astragali* Radix and the *Salvia Miltiorrhizae* Radix to be mixed before performing an extraction process, the *Astragali* Radix and the *Salvia Miltiorrhizae* Radix may be preferably mixed with each other at a weight ratio of 9:1 to 1:9, more preferably, a weight ratio of 1:1. When a mixed ratio between the *Astragali* Radix and the *Salvia Miltiorrhizae* Radix is out of the above-described range, there is no large difference in effects of treatment or prevention on the oxidative brain damage and brain dysfunction as compared to a case in which each extract of *Astragali* Radix and *Salvia Miltiorrhizae* Radix is used alone, and when the *Astragali* Radix and the *Salvia Miltiorrhizae* Radix are mixed at the above-described mixed ratio, the best effect is shown.

The extract of the present invention may be prepared by extraction with an extraction solvent, or may be prepared by adding a fraction solvent to an extract obtained by extraction with an extraction solvent, followed by fraction. The extraction solvent may be at least one kind selected from the group consisting of water and organic solvents. The organic solvent may be a polar solvent including C1 to C5 alcohols such as methanol, ethanol, or the like, ethyl acetate, acetone, or the like, a non-polar solvent including hexane or dichloromethane, or mixtures thereof, and the fraction solvent may be water, butanol, ethyl acetate, chloroform, hexane or mixtures thereof.

In the composition of the present invention, the extraction solvent for the extract of *Astragali* Radix and *Salvia Miltiorrhizae* Radix is preferably 20% to 40% ethanol, more preferably, 30% ethanol. By extracting the composition with 20% to 40% ethanol which is an extraction solvent, destruction of the active ingredient of the extract included in the composition according to the present invention may be controlled and high yield of an active ingredient may be obtained. In an exemplary embodiment of the present invention, as a result from comparison between a composition including an extract with 30% ethanol and a composition including an extract with distilled water in view of antioxidant capacity, it could be confirmed that the extract with 30% ethanol had higher antioxidant capacity as compared to the extract with distilled water.

After the extraction or the fraction process is performed, the extract may be concentrated by performing reduced pressure filtration or by performing additional concentration and/or lyophilization or solvent may be removed. The obtained extract may be stored in a deep freezer until used.

The composition for preventing or treating oxidative brain damage and brain dysfunction of the present invention may include an extract of *Astragali* Radix and *Salvia Miltiorrhizae* Radix as an active ingredient in an amount of 0.001 to 99.99 wt %, preferably, 0.1 to 99 wt % based on a total weight of the composition. In addition to the extract of *Astragali* Radix and *Salvia Miltiorrhizae* Radix, the composition may additionally contain nutritional supplement, vitamins, electrolytes, flavoring agents, coloring agents, enhancers, pectic acid and salts thereof, alginic acid and salts thereof, organic acids, protective colloidal thickeners, pH adjusting agents, stabilizers, preservatives, glycerin, alcohol, carbonization agents used in carbonated beverages, and the like, and these ingredients may be independently added to the composition or may be added combination with the composition.

The composition including the extract of *Astragali* Radix and the *Salvia Miltiorrhizae* Radix may further include a suitable carrier, an excipient and a diluent which are generally used in preparation of the composition.

The composition of the present invention may be parenterally administered (for example, intravenous, subcutaneous, intraperitoneal, or topical administration), or orally administered according to target methods. Preferable dosage may vary depending on condition, body weight, degree of diseases, drug formulation, administration route and period, and may be appropriately selected by a person skilled in the art. Preferably, the composition for treatment of the present invention is preferably administered in an amount of 0.0001 to 1000 mg/kg per one day, more preferably, 0.01 to 100 mg/kg per one day, based on an amount of the extract of *Astragali* Radix and the *Salvia Miltiorrhizae* Radix. The administration may be performed once a day and may be divided and administered several times. The above-described dosage and administration frequency are not intended the scope of the invention in any aspect.

In another general aspect, a preparation method of a composition for preventing or treating oxidative brain damage and brain dysfunction includes:

extracting a mixture of *Astragali* Radix and *Salvia Miltiorrhizae* Radix with 10 to 70% ethanol; and lyophilizing the extract.

In the preparation method, the *Astragali* Radix and the Salvia Miltiorrhizae Radix may be mixed with each other at a weight ratio of 9:1 to 1:9, more preferably, a weight ratio of 1:1. In addition, in the extracting of a mixture of *Astragali* Radix and *Salvia Miltiorrhizae* Radix with 20% to 40% ethanol, 30% ethanol is preferably used. When a mixed ratio between the *Astragali* Radix and the *Salvia Miltiorrhizae* Radix is out of the above-described range, there is no large difference in the effects of treatment or prevention on the oxidative brain damage and brain dysfunction as compared to a case in which each extract of *Astragali* Radix and *Salvia Miltiorrhizae* Radix is used alone, and when the *Astragali* Radix and the *Salvia Miltiorrhizae* Radix are mixed at the above-described mixed ratio, the best effect is shown.

The preparation method of the composition for preventing or treating oxidative brain damage and brain dysfunction according to the present invention includes the extracting of a mixture of *Astragali* Radix and *Salvia Miltiorrhizae* Radix with 20% to 40% ethanol, such that destruction of the active ingredient of the extract of *Astragali* Radix and *Salvia*

Miltiorrhizae Radix included in the composition according to the present invention may be controlled and high yield of active ingredient may be obtained.

In another general aspect, a food composition for preventing or improving oxidative brain damage and brain dysfunction includes an extract of *Astragali* Radix and *Salvia Miltiorrhizae* Radix as an active ingredient. In addition, in another general aspect, a preparation method of food composition for preventing or improving oxidative brain damage and brain dysfunction includes: extracting a mixture of *Astragali* Radix and *Salvia Miltiorrhizae* Radix with 10 to 70% ethanol; and lyophilizing the extract.

In the present specification, a food means a natural product or processed products containing one or more nutrients, preferably, is directly edible through processing processes to some degree, and in general, includes all of health Food, beverage, and food and beverage additives.

The extract of *Astragali* Radix and *Salvia Miltiorrhizae* Radix in the food composition according to the present invention may have a content of 0.0001 to 10 wt % based on total food composition, and the food may be formulated as drinks, caramel, chocolate, diet bars, or snacks by using generally used ingredients.

The food composition may further include a food auxiliary additive which is acceptable as a food, and may further include a suitable carrier, an excipient and a diluent which are generally used in preparation of food.

Advantageous Effects

The composition including an extract of *Astragali* Radix and *Salvia Miltiorrhizae* Radix as an active ingredient according to the present invention has a highly outstanding preventive or therapeutic effect in animal models simulating brain-tissue damage and brain dysfunction induced by acute and long-term excessive stress generated in actual clinical practice, which is effectively usable as a therapeutic agent.

BEST MODE

Hereinafter, the present invention will be described in detail with reference to Examples. However, these examples are only to illustrate the present invention and the scope of the present invention is not construed to be limited to these examples. In addition, it is obvious to those skilled in the art that various modifications, alterations, and changes may be made without departing from the spirit and the scope of the present invention.

EXAMPLE 1

Figure 1:
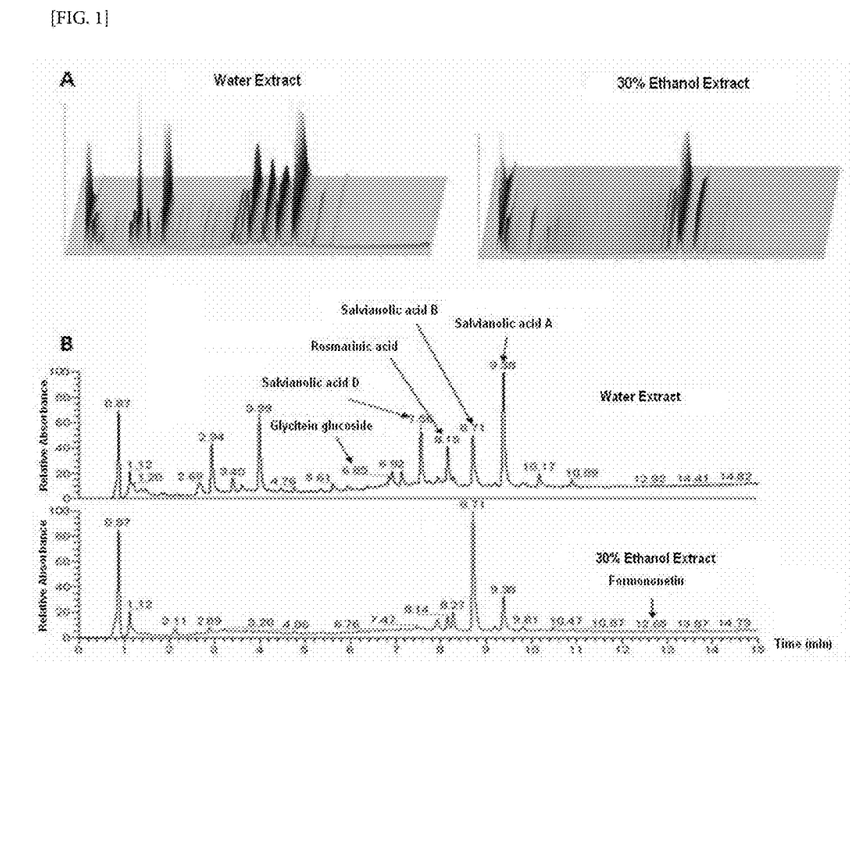
FIGS. 1A and 1B illustrate a drug fingerprint using two compositions including extracts obtained by using distilled water and ethanol and index materials.

Preparation of Composition Containing Extract of *Astragali* Radix and *Salvia Miltiorrhizae* Radix and Evaluation of Antioxidant Capacity According to Extraction Solvents 1-1. Preparation of Composition Using Distilled Water and Ethanol as Extraction Solvent Mixtures each containing 1 part by weight of *Astragali* Radix and 1 part by weight of *Salvia Miltiorrhizae* Radix were extracted with distilled water by hot water extraction and with 30% ethanol, followed by filtration, centrifugation, and lyophilization. Finally, about 20.5% and 18.0% of dried extracts based on weights of dry compositions before decoction process were obtained, respectively. In order to confirm differences in quality control with respect to ingredients of recovered dried extract and ingredient analysis with respect to each extract, a drug fingerprint was made by using two kinds of herbal medicines configuring the composition of the present invention and index materials (*Astragali* Radix: astragaloside IV, formonoetin; *Salvia Miltiorrhizae* Radix: rosmarinic acid, Salvianolic acid B) through HPLC (FIG. 1).

1-2. Evaluation of Antioxidant Capacity According to Extraction Solvents

Each content of compounds (*Astragali* Radix: Astragaloside IV, formonoetin; *Salvia Miltiorrhizae* Radix: rosmarinic acid, Salvianolic acid B) which are determined as active ingredients in components of each composition prepared by Example 1-1 was analyzed and results thereof were shown in Table 1 below.

TABLE 1

Analysis of Content of Active Ingredients in Extracts Obtained by Using Distilled Water and 30% Ethanol

|  | Astragali Radix (content %) | | *Salvia Miltiorrhizae* Radix (content %) | | Astragali Radix and *Salvia Miltiorrhizae* Radix (content %) | |
| --- | --- | --- | --- | --- | --- | --- |
|  | Water Extract | 30% Ethanol Extract | Water Extract | 30% Ethanol Extract | Water Extract | 30% Ethanol Extract |
| Astragaloside IV | 0.081 ± 0.000 | 0.0161 ± 0.004 | Not Detected | Not Detected | 0.024 ± 0.004 | 0.087 ± 0.004 |
| Formononetin | 0.007 ± 0.001 | 0.077 ± 0.000 | Not Detected | Not Detected | 0.002 ± 0.001 | 0.021 ± 0.001 |
| Rosmarinic acid | Not Detected | Not Detected | 0.246 ± 0.001 | 0.253 ± 0.001 | 0.136 ± 0.002 | 0.103 ± 0.002 |
| Salvianolic acid B | Not Detected | Not Detected | 8.08 0.136 | 8.689 ± 0.187 | 0.631 ± 0.012 | 3.621 ± 0.038 |

Figure 2:
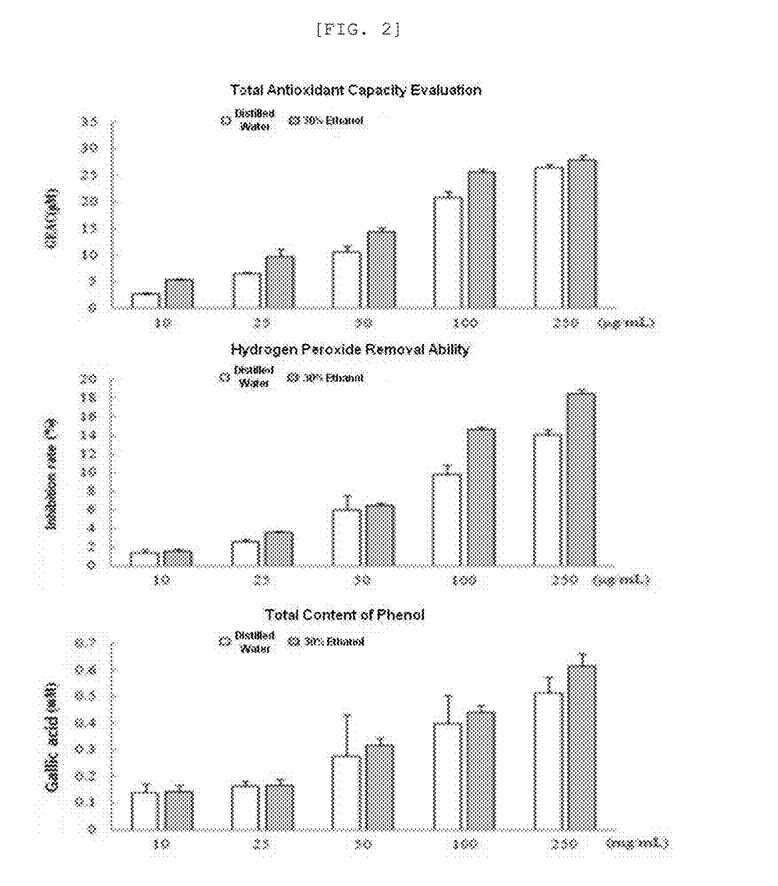
FIG. 2 is a graph showing each antioxidant efficacy of the distilled water extract and the ethanol extract.

As a result obtained by evaluating an antioxidant capacity of each composition prepared by Example 1-1, that is, between the compositions extracted with distilled water and 30% ethanol through total antioxidant capacity, hydrogen peroxide removal capacity, and total phenol content, it could be confirmed that the composition of the present invention which was extracted with 30% ethanol had more excellent antioxidant capacity than the composition extracted with water (FIG. 2).

EXAMPLE 2

Evaluation of Efficacy on Prevention and Treatment Against Oxidative Damage to Brain Tissue 2-1. Efficacy Assay with Respect to Oxidative Damage to Brain Tissue Induced by Stress 60 of 5-week-old male rats (SD rat, 180-200 g) were divided into six groups (10 rats per each group), and then distilled water, three concentrations (50, 100, 200 mg/kg) of the composition of the present invention and vitamin C (100 mg/kg) were orally administered to five groups except for one normal group, once a day for three days before stress induction. (Hereinafter, each group in the drawings showing each experimental result was represented by a normal group—Normal, a control group (distilled water)—Control, three concentrations of compositions of the present invention—Myp 50, Myp 100, Myp 200, vitamin C-Vit C100, respectively. In addition, the composition of the present invention may be represented by Myelophil). Then, after extreme mental stress is applied to the rats by removing beards and eyebrows for 12 hours, brain tissue and blood were separated postmortem, and drug efficacy was evaluated with respect to a stress-related hormone in the serum, oxidative damage to the brain tissue, inflammation degree, and inflammation-related factors of the brain tissue. Results thereof were shown in FIGS. 3 to 5.

Figure 3:
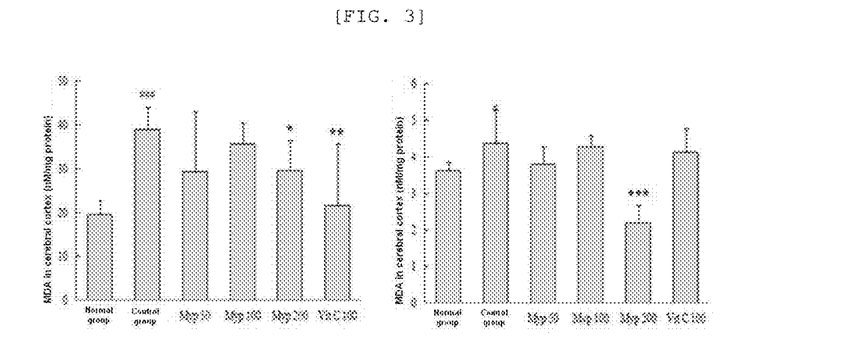
FIG. 3 is a graph showing each efficacy of the composition according to the present invention against oxidative damage in serum of rats induced by acute stress.
Figure 4:
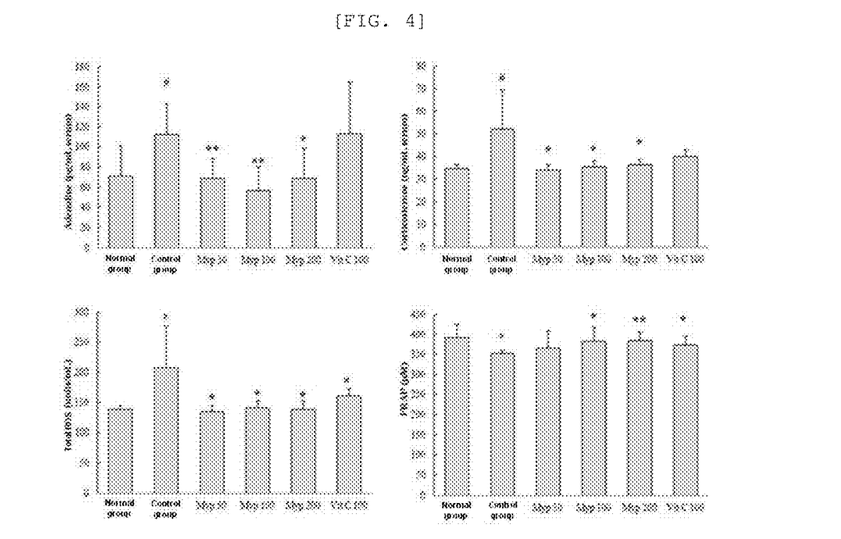
FIG. 4 is a graph showing efficacy of the composition of the present invention against lipid peroxidation in brain tissues (cerebrum and hippocampus) of rats induced by acute stress.
Figure 5:
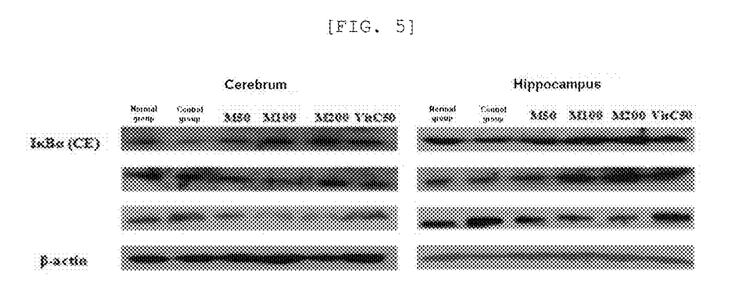
FIG. 5 illustrates images obtained by confirming efficacy and drug mechanism of inflammatory-related factors in the brain tissues (cerebral and hippocampus) of the rats induced by acute stress.

When evaluating the stress hormone in the serum, a stress-related hormone level was significantly reduced in the experimental group. In experiments evaluating oxidative damage, the experimental group to which the composition of the present invention was administered was significantly improved (FIG. 3). In addition, in experiments confirming oxidative damage to brain tissue and inflammation degree, the effect of the composition of the present invention was proven (FIG. 4). Further, when measuring the inflammation-related factors in brain tissues, that is, cerebral and hippocampus, respectively, in experiments confirming action mechanism of the drug, the experimental group showed significantly improved efficacy (FIG. 5).

2-2. Efficacy Assessment on Drug Preventing or Treating Oxidative Damage to Brain Tissue and Brain Dysfunction 48 of 10-week-old male C57 mice (C57/BL6, 24-27 g) were divided into six groups (8 rats per each group), and then distilled water, the composition of the present invention (50, 100, 200 mg/kg, P.O) and tacrine (10 mg/kg, P.O) were administered once a day to five groups except for one normal group for 1 week, then scopolamine (1 mg/kg, I.P) which is a chemical drug inducing memory loss and brain damage having oxidative mechanism was administered. First behaviors were observed and drug efficacy on the brain tissue against oxidative damage to the brain tissue and the brain dysfunction were evaluated. Results thereof were shown in FIGS. 6 and 7.

Figure 6:
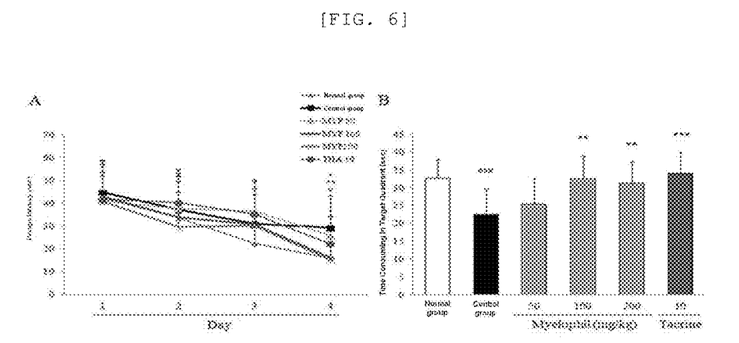
FIGS. 6A and 6B are graphs showing an improvement efficacy against memory impairment of the rats induced by acute stress.
Figure 7:
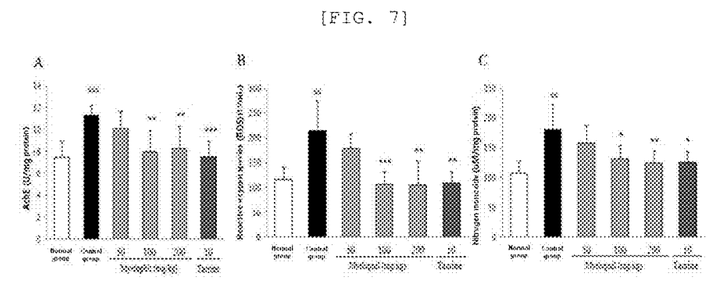
FIGS. 7A and 7B are graphs showing pharmacological action against memory impairment and an efficacy against oxidative brain damage of the composition according to the present invention in the rats induced by acute stress.

In experiments in respect to behavior observation and memory loss, the experimental group to which the composition of the present invention was administered showed significant improvement (FIG. 6). In addition, activities of enzymes related with oxidative damage in blood and brain tissue and memory loss performing important functions in brain were significantly improved in the experimental group to which the composition of the present invention was administered (FIG. 7).

EXAMPLE 3

Evaluation of Efficacy on Prevention and Treatment Against Oxidative Damage to Brain Tissue Induced by Chronic Stress 3-1. Efficacy Assay on the Composition of the Present Invention Against Oxidative Brain Damage and Brain Dysfunction Induced by Chronic Stress (Restraint Stress)

60 of 8-week-old male C57 mice (C57/BL6, 22-26 g) were divided into six groups (10 rats per each group), and then distilled water, the composition of the present invention (25, 50, 100 mg/kg, P.O) and vitamin C (100 mg/kg, P.O) were administered to five groups except for one normal group, once a day for three weeks, and after restraint stress, which is mental stress inducing brain damage, was induced for three hours once per day for three weeks, efficacy of the composition of the present invention against oxidative brain damage and brain dysfunction induced by the mental stress in the brain tissue and the blood serum was evaluated.

Figure 8:
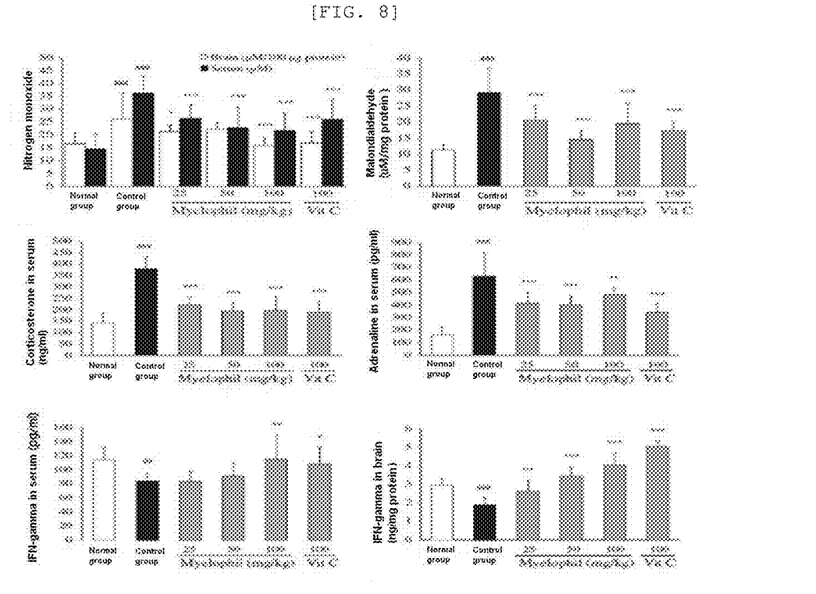
FIG. 8 is a graph showing an improvement efficacy against oxidative brain damage and an improvement effect against stress hormone hypersecretion of the composition according to the present invention in the rats induced by chronic restraint stress.
Figure 9:
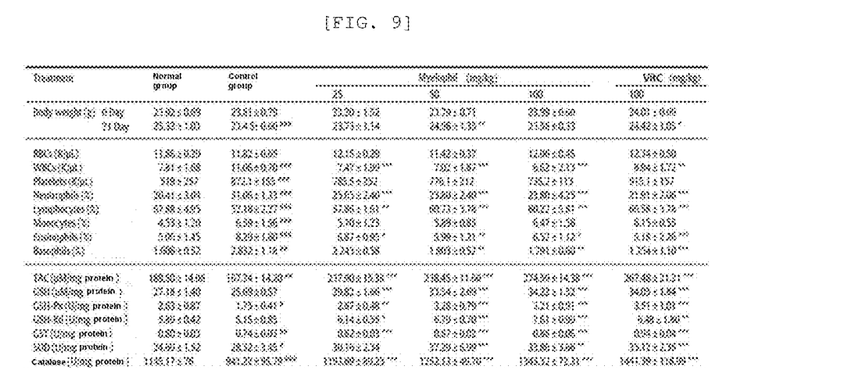
FIG. 9 is a Table showing hematological changes observation and antioxidant improvement efficacy against oxidative brain damage of the composition according to the present invention in rats induced by chronic stress.
Figure 10:
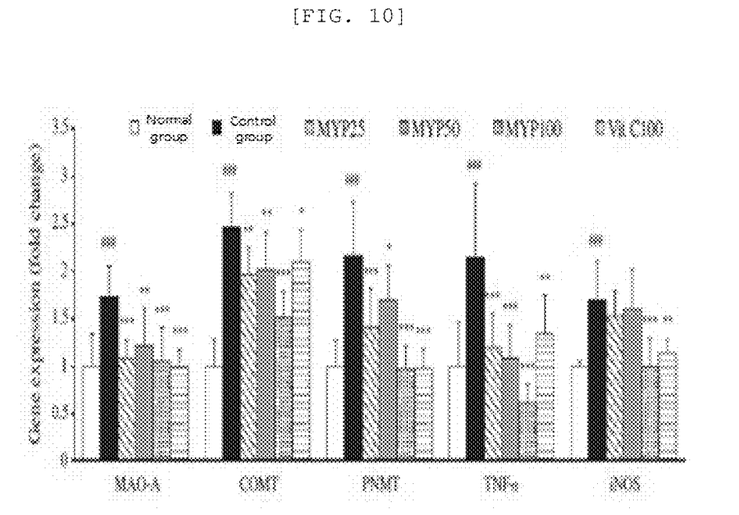
FIG. 10 is a graph showing change analysis of gene expressions with respect to stress hormone metabolization enzymes and inflammatory factors against oxidative brain damage of the composition according to the present invention in rats induced by chronic restraint stress.
Figure 11:
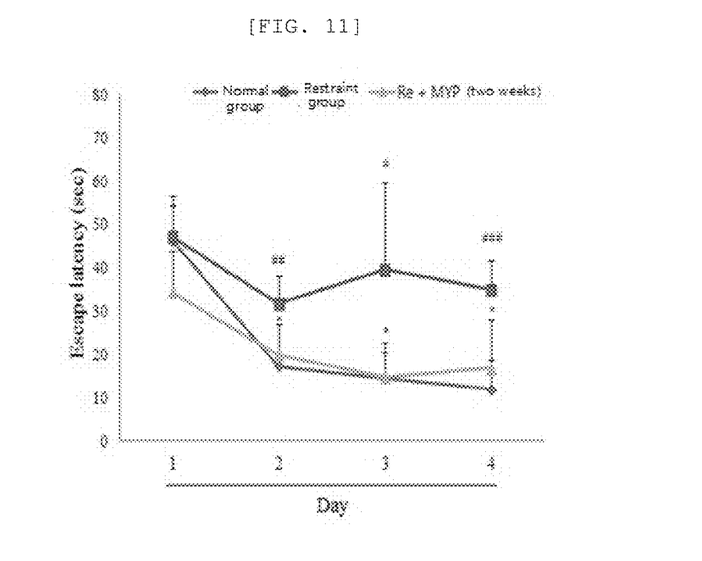
FIG. 11 is a graph showing an improvement effect against cognitive impairment of the composition according to the present invention.
Figure 12:
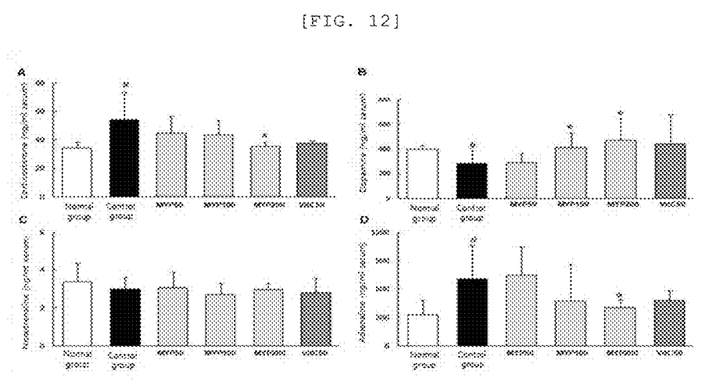
FIGS. 12A-12D are graphs showing an improvement effect of stress hormone secretion of the composition according to the present invention in rats induced by chronic cold stress.

In experiments in respect to stress hormone hypersecretion and oxidative brain damage, the experimental group to which the composition of the present invention was administered showed significant improvement (FIG. 8), and showed efficacy in improving antioxidant system in blood and brain tissue (FIG. 9), in improving factors related with oxidative damage in gene expression and protein level, and inflammation, and in improving stress hormone metabolism disorder. In addition, the experimental group to which the composition of the present invention was administered showed significantly improved effect against cognitive memory impairment (FIGS. 10 and 11).

3-2. Efficacy Assay on the Composition of the Present Invention Against Oxidative Brain Damage Induced by Chronic Stress (Cold Stress)

60 of 5-week-old male albinic rats (Balb/C, 18-20 g) were divided into six groups (8 rats per each group), and then distilled water, the composition of the present invention (25, 50, 100 mg/kg, P.O) and vitamin C (50 mg/kg, P.O) were administered to five groups except for one normal group, once a day for two weeks, and after cold stress was induced for four hours once per day for two weeks, efficacy of the composition of the present invention against oxidative brain damage induced by the mental stress in the brain tissue and the blood serum was confirmed in protein and gene level.

Figure 13:
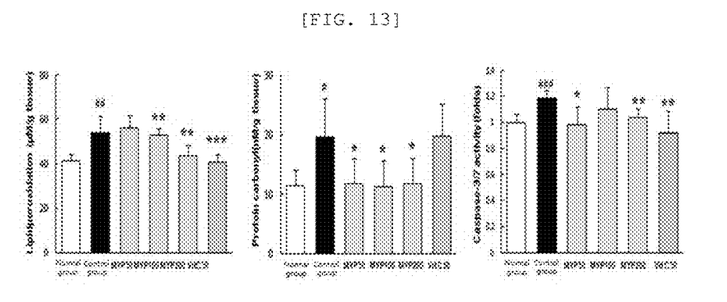
FIG. 13 is a graph showing an improvement effect against oxidative brain damage of the composition according to the present invention in brain tissue of the rats induced by chronic cold stress.
Figure 14:
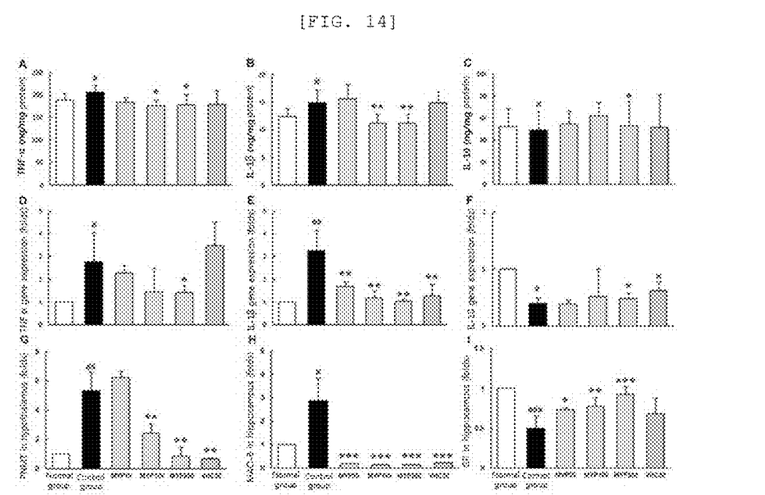
FIGS. 14A-14I are graphs showing an improvement effect with respect to an inflammatory reaction and enzymes related with hormone metabolism of the composition according to the present invention in the brain tissues of the rats induced by chronic stress.
Figure 15:
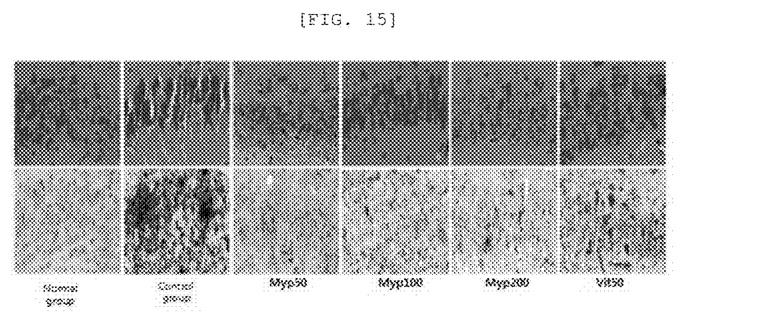
FIG. 15 is images showing histologic improvement against lesions of brain tissue induced by chronic stress the composition according to the present invention.

In experiments in respect to stress hormone hypersecretion and oxidative brain damage, the experimental group to which the composition of the present invention was administered showed significant improvement (FIGS. 12 and 13), and showed improvement in factors related with oxidative damage in gene expression and protein level and inflammation in blood and brain tissue (FIG. 14). In particular, it could be confirmed that cell death observed in hippocampus was significantly improved in the experimental group to which the composition of the present invention was administered (FIG. 15).

Hereinafter, preparation examples for compositions of the present invention are provided.

PREPARATION EXAMPLE 1

Preparation Using Extract of *Astragali* Radix and *Salvia Miltiorrhizae* Radix

Preparation Example 1

Preparation of Powder

Powder of extract of *Astragali* Radix and *Salvia Miltiorrhizae* Radix 20 mg
Lactose 100 mg
Talc 10 mg These ingredients were mixed with each other and filled in an air-tight container to prepare the powder.

Preparation Example 2

Preparation of Tablet

Powder of extract of *Astragali* Radix and *Salvia Miltiorrhizae* Radix 10 mg [87] Corn starch 100 mg
Lactose 100 mg
Magnesium stearate 2 mg These ingredients were mixed with each other and pressed according to general tablet preparation method to prepare a tablet.

Preparation Example 3

Preparation of Capsule

Extract of *Astragali* Radix and *Salvia Miltiorrhizae* Radix 10 mg
Crystalline cellulose 3 mg
Lactose 14.8 mg
Magnesium stearate 0.2 mg According to general capsule preparation method, these ingredients were mixed with each other and filled in a gelatin capsule to prepare a capsule.

Preparation Example 4

Preparation of Injection

Extract of *Astragali* Radix and *Salvia Miltiorrhizae* Radix 10 μg/ml
The maximum BP of 1 ml of sodium chloride for injection until BP of diluted hydrochloric acid has a pH of 3.5.

These ingredients were mixed with each other according to general injection preparation, a solvent was filled in 5 ml ampoule made of transparent glass, and sealed in upper air lattice by melting the glass, followed by autoclave sterilization at 120° C. for 15 minutes or more for sterilization to prepare an injection.

PREPARATION EXAMPLE 2

Preparation of Drink

Extract of *Astragali* Radix and *Salvia Miltiorrhizae* Radix 100 mg
Glucose 10 mg After 0.6 g of citric acid and 25 g of liquid phase oligosaccharide were mixed, 300 ml purified water was added to the mixture and 200 ml of the obtained mixture was filled in each bottle. The filled bottles were sterilized at 130° C. for 4 to 5 seconds to prepare a drink.

The invention claimed is:

1. A composition for treating oxidative brain damage and brain dysfunction comprising:
   an extract of *Astragali* Radix and *Salvia Miltiorrhizae* Radix as an active ingredient, wherein a weight ratio between the *Astragali* Radix and the *Salvia Miltiorrhizae* Radix is 9:1 to 1:9,
   wherein the extract of *Astragali* Radix and the *Salvia Miltiorrhizae* Radix is extracted with 20% to 40% ethanol, and
   wherein the oxidative brain damage and the brain dysfunction are at least any one selected from the group consisting of Alzheimer syndrome, Parkinson syndrome, and Huntington syndrome.

2. The composition of claim 1, wherein the active ingredient is Astragaloside IV, Formononetin, Rosmarinic acid, or Salvianolic acid B.

3. A food composition for improving oxidative brain damage and brain dysfunction comprising:
   an extract of *Astragali* Radix and the *Salvia Miltiorrhizae* Radix as an active ingredient, wherein a weight ratio between the *Astragali* Radix and the *Salvia Miltiorrhizae* Radix is 9:1 to 1:9, wherein the extract of *Astragali* Radix and the *Salvia Miltiorrhizae* Radix is extracted with 20% to 40% ethanol, and wherein the oxidative brain damage and the brain dysfunction are at least any one selected from the group consisting of Alzheimer syndrome, Parkinson syndrome, and Huntington syndrome.

4. The food composition of claim 3, wherein the active ingredient is Astragaloside IV, Formononetin, Rosmarinic acid, or Salvianolic acid B.

5. A preparation method of a composition for treating oxidative brain damage and brain dysfunction comprising:

extracting a mixture of *Astragali* Radix and *Salvia Miltiorrhizae* Radix with 20% to 40% ethanol; and lyophilizing the extract, wherein a weight ratio between the *Astragali* Radix and the *Salvia Miltiorrhizae* Radix in the mixture of *Astragali* Radix and *Salvia Miltiorrhizae* Radix is 9:1 to 1:9, and wherein the oxidative brain damage and the brain dysfunction are at least any one selected from the group consisting of Alzheimer syndrome, Parkinson syndrome, and Huntington syndrome.

\* \* \* \* \*